United States Patent [19]

Paumard et al.

[11] Patent Number: 5,024,983

[45] Date of Patent: Jun. 18, 1991

[54] CATALYST SYSTEM, PROCESS FOR ITS PREPARATION AND ITS APPLICATION TO THE MANUFACTURE OF ALDEHYDES

[75] Inventors: Eric Paumard, Cappel; Sylvain Mutez, Tourcoing; André Mortreux, Hem; Francis Petit, Villeneuve D'Ascq, all of France

[73] Assignee: Norsolor, Paris, France

[21] Appl. No.: 323,718

[22] Filed: Mar. 15, 1989

[30] Foreign Application Priority Data

Mar. 30, 1988 [FR] France ................... 88 04192

[51] Int. Cl.$^5$ .................... B01J 31/22; B01J 31/24
[52] U.S. Cl. .................... 502/167; 502/162; 204/59 R; 204/59 QM; 568/455; 568/454
[58] Field of Search ............. 502/162, 167; 204/59 R, 204/59 QM

[56] References Cited

U.S. PATENT DOCUMENTS

| | | | |
|---|---|---|---|
| 3,959,386 | 5/1976 | Pinxe ................... | 502/162 X |
| 4,408,078 | 10/1983 | Van Leeuwen et al. ........ | 502/169 X |
| 4,608,444 | 8/1986 | Jacobson ................. | 568/462 |
| 4,668,651 | 5/1987 | Billie et al. ............. | 502/162 X |
| 4,776,987 | 10/1988 | Luft et al. .............. | 502/102 X |
| 4,877,908 | 10/1989 | Petit et al. ............. | 568/814 |

*Primary Examiner*—Patrick P. Garvin

*Attorney, Agent, or Firm*—Finnegan, Henderson, Farabow, Garrett & Dunner

[57] ABSTRACT

The catalyst system is characterized in that it comprises:
at least one platinum complex of formula $LPtX_2$ in which L is an organic compound containing at least two phosphorus atoms capable of coordinating platinum and X is a halogen atom, and
at least one combination formed between iron and an alkene carbonate, the alkene group preferably containing from 2 to 6 carbon atoms.

The process for its preparation is characterized in that at least one combination formed between iron adn the alkene carbonate is reacted with at least one platinum complex of formula $LPtX_2$ in at least one solvent for the said complex, at a temperature of between 10° C. and the boiling point of the said solvent. The combination of iron and of an alkene carbonate may be formed by electrochemical reduction.

Application of the catalyst system to the manufacture of aldehydes by hydroformylation of an organic compound containing ethylenic unsaturation, consisting in reacting the said organic compound with a mixture of carbon monoxide and hydrogen in the presence of an effective quantity of the said catalyst system, at a temperature of between 10° and 300° C. and at a pressure of between 10 and 350 bars.

12 Claims, No Drawings

CATALYST SYSTEM, PROCESS FOR ITS PREPARATION AND ITS APPLICATION TO THE MANUFACTURE OF ALDEHYDES

The present invention relates to a catalyst system, a process for its preparation and its application to the manufacture of aldehydes by hydroformylation of organic compounds containing ethylenic unsaturation.

The purpose of the present invention consists in obtaining, by hydroformylation of compounds containing ethylenic unsaturation, a mixture of normal and branched aldehydes in which the proportion of normal aldehydes is as high as possible.

A first subject matter of the present invention consists of a catalyst system characterized in that it comprises:
  at least one platinum complex of formula $LPtX_2$ in which L is an organic compound containing at least two phosphorus atoms capable of coordinating platinum and X is a halogen atom, and
  at least one combination formed between iron and an alkene carbonate, the alkene group preferably containing from 2 to 6 carbon atoms.

In the catalyst system according to the present invention the platinum complex and the iron-based combination are preferably present in respective proportions such that the atomic ratio Fe/Pt is between 0.2 and 5.

The catalyst system according to the invention comprises, as first component, at least one platinum complex of formula $LPtX_2$ in which X may be chosen in any manner from fluorine, chlorine, bromine and iodine. The organic phosphorus compound L may be, for example:

a bis(diphenylphosphino)alkane of formula

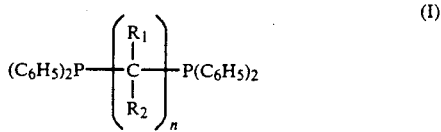

(I)

in which $R_1$ and $R_2$, which are identical or different, are chosen from the hydrogen atom and aliphatic hydrocarbon radicals, the latter containing functional groups and/or being bonded to each other if appropriate, and n is greater than or equal to 4;

an aminophosphinephosphinite of formula

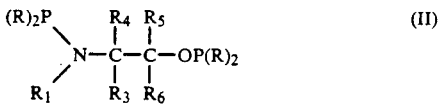

(II)

in which:

R is an aliphatic, cycloaliphatic or aromatic hydrocarbon radical, $R_1$ is chosen from the hydrogen atom and hydrocarbon radicals, $R_3$ and $R_4$, necessarily differ from each other, are chosen from the hydrogen atom and hydrocarbon radicals, optionally carrying at least one functional group chosen from the alcohol, thiol, thioether, amine, imine, acid, ester, amide and ether functional groups, and $R_5$ and $R_6$ are chosen from the hydrogen atom and hydrocarbon radicals which optionally contain functional groups, and $R_1$, $R_3$ and the nitrogen and carbon atoms which carry them respectively may together form a heterocyclic ring.

(1S,2S) (+) Trans-1,2-bis(diphenylphosphinomethyl)cyclohexane, 1,4-bis(diphenylphosphino)butane and isopropylidene-2,3-dihydroxy-1,4-bis(diphenylphosphino)butane constitute examples of organic phosphorus compounds of formula (I) which may be employed within the scope of the present invention. Furthermore, certain compounds of formula (II) and the method of their preparation have been described in French Patent Application No. 2,550,201, published Feb. 8, 1985, which corresponds to U.S. Pat. No. 4,877,908.

The catalyst system according to the invention additionally comprises at least one combination formed between iron and an alkene carbonate such as propylene carbonate, ethylene carbonate, 1,2-butylene carbonate and 1,2-hexylene carbonate.

The said combination may be formed by reduction of an electrochemical solvent comprising at least one alkene carbonate in an electrochemical cell comprising an iron anode, a cathode and a reference electrode, by raising the cathode to a potential lower than or equal to approximately −1 volt relative to the reference electrode, and by imposing this potential for a sufficient period of time to ensure the production of the desired quantity of the said combination. The reference electrode may be chosen from known electrodes such as especially $Ag/AgCl/Cl^-$, $Ag/Ag^+$, $Hg/Hg_2Cl_2$ (calomel). According to an embodiment of the present invention, the reduction of the electrochemical solvent may be performed in the presence of a small quantity of a conductive salt soluble in the electrochemical solvent, such as, for example, tetra-n-butylammonium hexafluorophosphate. The presence of this conductive salt makes it advantageously possible to accelerate the reduction of the solvent, particularly at moderate temperature. The electrochemical reduction stage according to the invention is generally performed at a temperature of between 10° C. and approximately 70° C. and while the electrochemical cell is kept under an inert gas atmosphere such as nitrogen. The electrochemical solvent employed within the scope of the present invention necessarily comprises at least one alkene carbonate such as defined above. It may additionally comprise, mixed with the latter, another solvent such as, for example, an aromatic hydrocarbon (benzene, toluene, xylenes, and the like). Another method of preparation of the said combination consists in reducing an electrochemical solvent comprising at least one alkene carbonate in an electrochemical cell comprising an iron anode and a cathode, between which a potential difference higher than or equal to approximately 10 volts is applied, and in maintaining this potential difference for a sufficient period of time to ensure the production of the desired quantity of the said combination. As in the previous method of preparation, the iron anode is gradually dissolved.

As examples of cathodes which can be employed in this process, there may be mentioned, on the one hand, graphite cathodes and, on the other hand, cathodes of a metal which cannot be degraded by the electrochemical solvent, such as platinum or stainless steel.

A second subject matter of the present invention consists of a process for the preparation of a catalyst system such as described above. A process of this kind consists in reacting at least one combination formed between iron and the alkene carbonate with at least one platinum complex of formula $LPtX_2$ in at least one solvent for the said complex, at a temperature of between 10° C. and the boiling point of the said solvent. Among the solvents for the platinum complex of formula $LPtX_2$ there may be mentioned in particular aromatic hydrocarbons (such as, for example, benzene, toluene and xylenes) and alkene carbonates, especially those in which the alkene group contains from 2 to 6 carbon atoms. To implement the process according to the invention, it will be preferred to employ a solvent comprising at least approximately 10% by volume of alkene carbonate. The duration of the reaction between the iron-based combination and the platinum complex can vary, according to the usual rules which are well known to the person skilled in the art, as a function of the reaction temperature which is chosen and of the concentration of the active species in the solvent. By way of example, this duration generally does not exceed 20 minutes when the reaction temperature is 80° C.

A number of embodiments can be envisaged within the scope of the process according to the present invention. A first embodiment consists in forming a combination of iron and of an alkene carbonate, for example by one of the electrochemical methods described above, and in then introducing the platinum complex into the medium in which the iron combination has been formed, said medium already comprising the solvent needed for the reaction. A second embodiment consists in forming a combination of iron and of an alkene carbonate, for example by one of the electrochemical methods described above, in isolating (in the form of powder) the said combination from the medium in which it has been formed (for example by filtering, washing and drying the precipitate which forms in the electrochemical cell), and in then introducing the said powder into a solution of the platinum complex in the solvent needed for the reaction. Finally, a third embodiment consists in forming the combination of iron and of an alkene carbonate in the presence of the solvent and of the platinum complex, for example by one of the electrochemical methods described above; in this case, the operation is carried out for a sufficient period of time to ensure the production of a quantity of electricity equal to at least 0.2 faradays per gram/atom of platinum.

Whatever the embodiment chosen for the process according to the invention, it is desirable for the concentration of the platinum complex in the solvent for the reaction to be approximately between 0.001 and 0.2 moles per liter.

A third subject matter of the present invention consists of the application of the catalyst system described above to the manufacture of aldehydes by hydroformylation of an organic compound containing ethylenic unsaturation, characterized in that the said organic compound is reacted with a mixture of carbon monoxide and hydrogen in the presence of an effective quantity of the said catalyst system, at a temperature of between 10° C. and approximately 300° C. and at a pressure of between 10 and approximately 350 bars. An effective quantity of catalyst system is generally such that the molar ratio of the organic compound containing ethylenic unsaturation to the platinum is between 100 and 10,000.

The molar ratio $CO/H_2$ in the mixture of carbon monoxide and hydrogen involved in the hydroformylation reaction according to the invention is generally approximately between 0.5 and 2.

Among the organic compounds containing ethylenic unsaturation which can be subjected to the hydroformylation reaction according to the invention there may be mentioned in particular:
- olefins containing from 2 to 12 carbon atoms, such as especially propylene, 1-butene, 1-hexene, 4-methyl-1-pentene, 1-octene and the like,
- vinylaromatic compounds such as styrene, alphamethylstyrene, and the like, and
- dienes, such as, for example, 4-vinylcyclohexene.

The duration of the hydroformylation reaction according to the invention is generally approximately between 0.5 and 30 hours, depending on the pressure and temperature which are chosen.

The examples below are given by way of illustration of the present invention, no limitation being implied.

EXAMPLE 1

Preparation of Catalyst System 50 mg of $LPtCl_2$ complex, the ligand L being isopropylidene-2,3-dihydroxy-1,4-bis(diphenylphosphino)-butane, are introduced under nitrogen into a glass electrochemical cell, followed by the solvent consisting of a mixture of 15 cm$^3$ of benzene and of 10 cm$^3$ of propylene carbonate. After the catalyst has dissolved completely, the cathode (consisting of a platinum basket) and the anode (consisting of an iron cylinder) are immersed in the solvent, followed by the reference electrode (Ag-/AgCl/N(C$_4$H$_9$)$_4$Cl 0.1 M in propylene carbonate. With the temperature equal to 20° C., the reduction potential is set at $-1.85$ volts and the quantity of current passing through the circuit is measured with a coulometer. The quantity of iron needed for the reaction is measured by weighing the anode before and after the reduction (the mass obtained by weighing is generally identical with that determined from the number of coulombs flowing through the circuit). Under these conditions, the atomic ratio Fe/Pt is equal to 1.

EXAMPLE 2

Hydroformylation of Styrene

The catalyst system of Example 1 is introduced into a 100 cm$^3$ stainless steel autoclave reactor equipped with a stirring system using a bar magnet, and 0.68 grams of styrene are then added. The reactor is heated up to a temperature of 90° C. after the synthesis gas, consisting of an equimolar measure of carbon monoxide and hydrogen, has been charged. Finally, the mixture is stirred and the reaction is continued at 90° C. at a pressure of 100 bars for a time t (expressed in hours). A mixture comprising ethylbenzene, 2-phenylpropanal and 3-phenylpropanal is then obtained with a degree of conversion DC (expressed in percent). The analysis of this mixture makes it possible to determine, on the one hand, the proportion by weight of ethylbenzene EB (expressed in percent) and, on the other hand, the molar ratio n/b of the normal aldehyde to the branched aldehyde. The table below summarizes the results obtained as a function of the catalyst system employed.

EXAMPLES 3 to 8

A solvent consisting of a mixture of benzene and of propylene carbonate is introduced under nitrogen into a glass electrochemical cell. The solvent employed in Example 3 comprises 25 cm$^3$ of a mixture containing 60% of benzene. The solvent employed in Examples 4 and 8 comprises 18 cm$^3$ of a mixture containing 75% of benzene. The solvent employed in Examples 5 and 6 comprises 25 cm$^3$ of a mixture containing 75% of benzene. The solvent employed in Example 7 comprises 25 cm$^3$ of a mixture containing 89% of benzene. The cathode (consisting of a platinum basket) and the anode (consisting of an iron cylinder) are immersed in this solvent. With the temperature equal to 20° C., the potential difference between the anode and cathode is set at 60 volts. Progressive formation of a greenish-colored precipitate is observed. This is isolated by filtration and is purified by washing. The powder thus obtained is subjected to an elemental analysis by weight which gives the following results:

| | |
|---|---|
| C | 28% |
| H | 4% |
| O | 34% |
| Fe | 29% |

After the reactor described in Example 2 has been degassed, the complex LPtCl$_2$ is introduced into this reactor, with nitrogen purging, the ligand L being:
isopropylidene-2,3-dihydroxy-1,4-bis(diphenylphosphino)butane in the case of Examples 3 to 7 and
(S)-N-diphenylphosphino-2-(oxymethylenediphenylphosphino)pyrrolidine in the case of Example 8.

Into this reactor is then introduced, with stirring, the powder obtained before, in such quantity that the atomic ratio Fe/Pt is 1 (except for Examples 5 and 6, where this ratio has the values of 0.5 and 2.5 respectively), followed by styrene in such quantity that the molar ratio of styrene to the platinum is equal to 100. The reactor is then heated to a temperature of 90° C. after the synthesis gas, consisting of an equimolar mixture of carbon monoxide and hydrogen, has been charged, at a pressure of 100 bars. Stirring of the mixture is then commenced. After the reaction time t (expressed in hours) specified in the table below, the reactor is cooled and then the gas mixture is removed. The liquid phase recovered is analyzed by gas phase chromatography and the results obtained, expressed as in Example 2 above, are shown in the table below.

TABLE

| Example | t | DC | EB | n/b |
|---|---|---|---|---|
| 2 | 15 | 100 | 3 | 5.7 |
| 3 | 10 | 100 | 3 | 4.9 |
| 4 | 8 | 100 | 2.7 | 10.1 |
| 5 | 24 | 66 | 14 | 4.0 |
| 6 | 24 | 85 | 2.8 | 3.2 |
| 7 | 24 | 100 | 1.4 | 6.7 |
| 8 | 40 | 100 | 17 | 11.5 |

EXAMPLE 9

Hydroformylation of 1-hexene

Example 8 is reproduced, except that styrene is replaced with 1-hexene, the solvent comprises 25 cm$^3$ of a mixture containing 60% of benzene and the reaction time is 15 hours. A mixture comprising 15% by weight of hexane and 85% by weight of a mixture of n-heptanal, 2-methylhexanal and 2-ethylpentanal is obtained, with a degree of conversion of 100%, wherein the molar ratio n/b of normal aldehyde to branched aldehydes is equal to 11.5.

We claim:
1. Catalyst system comprising:
at least one platinum complex of formula LPtX$_2$ in which L is an organic compound containing at least two phosphorus atoms capable of coordinating platinum selected from (a) a bis(diphenylphosphino)-alkane of the formula

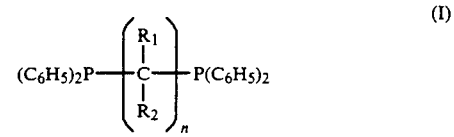

in which R$_1$ and R$_2$, which are identical or different, are chosen from the hydrogen atom and aliphatic hydrocarbon radicals, and n is greater than or equal to 4 and (b) an aminophosphinephosphinite of the formula

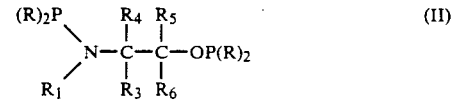

in which:
R is an aliphatic, cycloaliphatic or aromatic hydrocarbon radical,
R$_1$ is chosen from the hydrogen atom and hydrocarbon radicals,
R$_3$ and R$_4$ which necessarily differ from each other, are chosen from the hydrogen atom and hydrocarbon radicals optionally carrying at least one functional group chosen from alcohol, thiol, thioether, amine, imine, acid, ester, amide and ether functional groups,
R$_5$ and R$_6$ are chosen from the hydrogen atom and hydrocarbon radicals, and
R$_1$, R$_3$ and the nitrogen and carbon atoms which carry them respectively may together form a heterocyclic ring; and X is a halogen atom, and
at least one combination formed between iron and an alkene carbonate by electrochemical reduction.

2. Catalyst system according to claim 1, characterized in that the platinum complex and the iron-based combination are present in respective proportions such that the atomic ratio Fe/Pt is between 0.2 and 5.

3. Process for the preparation of a catalyst system according to claim 1, characterized in that at least one combination formed between iron and the alkene carbonate by electrochemical reduction is reacted with at least one platinum complex of formula LPtX$_2$ in at least one solvent for the said complex, at a temperature of between 10° C. and the boiling point of the said solvent.

4. Process of preparation according to claim 3, characterized in that the combination of iron and of an alkene carbonate is formed by reduction of an electrochemical solvent comprising at least one alkene carbonate in an electrochemical cell comprising an iron anode, a cathode and a reference electrode, by raising the cathode to a potential lower than or equal to −1 volt relative to the reference electrode and by imposing this potential for a sufficient period of time to ensure the production of the desired quantity of the said combination.

5. Process of preparation according to claim 3, characterized in that the combination of iron and of an alkene carbonate is formed by reduction of an electrochemical solvent comprising at least one alkene carbonate in an electrochemical cell comprising an iron anode and a cathode between which a potential difference higher than or equal to 10 volts is applied for a sufficient period of time to ensure the production of the desired quantity of the said combination.

6. Process according to either of claims 4 or 5, characterized in that the reduction of the electrochemical solvent is performed in the presence of a small quantity of a conductive salt soluble in the electrochemical solvent.

7. Process according to claim 4, characterized in that the reduction of the electrochemical solvent is performed at a temperature of between 10° C. and 70° C. and while the electrochemical cell is kept under an inert gas atmosphere.

8. Process according to claim 4, characterized in that the electrochemical solvent additionally comprises an aromatic hydrocarbon mixed with the alkene carbonate.

9. Process according to claim 3, characterized in that the solvent for the platinum complex is chosen from aromatic hydrocarbons and alkene carbonates.

10. Process according to claim 9, characterized in that the said solvent comprises at least 10% by volume of alkene carbonate.

11. Process according to claim 3, characterized in that the concentration of the platinum complex in the solvent for the reaction is between 0.001 and 0.2 moles per liter.

12. The catalyst system according to claim 1, wherein the alkene group of the alkene carbonate contains from 2-6 carbon atoms.

* * * * *